United States Patent
Mueller

(10) Patent No.: US 11,136,314 B2
(45) Date of Patent: Oct. 5, 2021

(54) FORMS OF AFATINIB DIMALEATE

(71) Applicant: Johnson Matthey Public Limited Company, London (GB)

(72) Inventor: Ronald Mueller, Devens, MA (US)

(73) Assignee: Johnson Matthey Public Limited Company, London (GB)

(*) Notice: Subject to any disclaimer, the term of this patent is extended or adjusted under 35 U.S.C. 154(b) by 0 days.

(21) Appl. No.: 16/593,581

(22) Filed: Oct. 4, 2019

(65) Prior Publication Data

US 2020/0039967 A1    Feb. 6, 2020

Related U.S. Application Data

(63) Continuation of application No. PCT/US2018/026383, filed on Apr. 6, 2018.

(60) Provisional application No. 62/482,456, filed on Apr. 6, 2017.

(51) Int. Cl.
    *C07D 405/12*      (2006.01)

(52) U.S. Cl.
    CPC ........ *C07D 405/12* (2013.01); *C07B 2200/13* (2013.01)

(58) Field of Classification Search
    CPC .................................................. C07D 405/12
    See application file for complete search history.

(56) References Cited

U.S. PATENT DOCUMENTS

| | | |
|---|---|---|
| 6,251,912 B1 | 6/2001 | Wissner et al. |
| RE43,431 E | 5/2012 | Himmelsbach |
| 9,758,471 B2 | 9/2017 | Verma et al. |
| 9,827,230 B2 | 11/2017 | Brisander et al. |
| 2005/0085495 A1 | 4/2005 | Soyka |
| 2018/0030038 A1 | 2/2018 | Jetti et al. |

FOREIGN PATENT DOCUMENTS

| | | | |
|---|---|---|---|
| EP | 3023421 A1 | 5/2016 | |
| WO | 2005037824 A2 | 4/2005 | |
| WO | 2009147238 A1 | 12/2009 | |
| WO | 2011003853 A2 | 1/2011 | |
| WO | 2012121764 A1 | 9/2012 | |
| WO | WO2012121764 * | 9/2012 | ........... C07D 405/12 |
| WO | 2013052157 A1 | 4/2013 | |
| WO | 2015103456 A1 | 7/2015 | |
| WO | 2016001844 A1 | 1/2016 | |
| WO | 2016027243 A1 | 2/2016 | |
| WO | 2016051380 A1 | 4/2016 | |
| WO | 2016079313 A1 | 5/2016 | |
| WO | 2016166720 A1 | 10/2016 | |
| WO | 2016185485 A2 | 11/2016 | |
| WO | 2016199076 A2 | 12/2016 | |
| WO | 2017033107 A1 | 3/2017 | |
| WO | 2017093789 A2 | 6/2017 | |

OTHER PUBLICATIONS

Caira, "Crystalline Polymorphism of Organic Compounds", Topics in Current Chemistry, Springer, Berlin, DE, Jan. 1, 1998, vol. 198, pp. 163-208.

* cited by examiner

*Primary Examiner* — Paul V Ward

(57) ABSTRACT

The present disclosure is directed to a crystalline, hydrated form of afatinib dimaleate having about 2 to 3 molecules of water, designated as Form Z, a pharmaceutical composition comprising the form, its method of use for treating a patient, and process for its preparation.

13 Claims, 3 Drawing Sheets

FORMS OF AFATINIB DIMALEATE

CROSS-REFERENCE TO RELATED APPLICATIONS

This application is a continuation of International Application No. PCT/US2018/026383, filed Apr. 6, 2018, which claims priority to U.S. Provisional Patent Application No. 62/482,546, filed on Apr. 6, 2017, the disclosures of which are incorporated herein by reference in their entireties for all purposes.

FIELD OF THE DISCLOSURE

The present disclosure relates to a novel form of afatinib dimaleate and processes for the preparation of the form. The present disclosure also relates to pharmaceutical compositions comprising the novel form of afatinib dimaleate and methods for treating disease using the form.

BACKGROUND OF THE DISCLOSURE

Afatinib, having the chemical designation (2E)-N-[4-(3-chloro-4-fluoroanilino)-7-[(3S)-oxolan-3-yl]oxy)quinoxazolin-6-yl]-4-(dimethylamino)but-2-enamide, or alternatively N-[4-[(3-chloro-4-fluorophenyl)amino]-7-[[(3S)-tetrahydro-3-furanyl]oxy]-6-quinazolinyl]-4-(dimethylamino)-2 butenamide, is an orally bioavailable inhibitor of the receptor tyrosine kinase (RTK) epidermal growth factor receptor (ErbB; EGFR) family, with antineoplastic activity. Afatinib has the following structure:

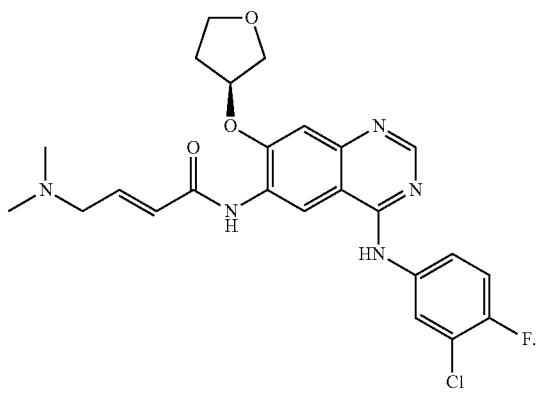 [SMILES: CN(C)C/C=C/C(=O)Nc1cc2c(Nc3ccc(F)c(Cl)c3)ncnc2cc1O[C@H]1CCOC1]

Afatinib is commercially marketed under the name GILOTRIF™ and is afatinib dimaleate having the following structure:

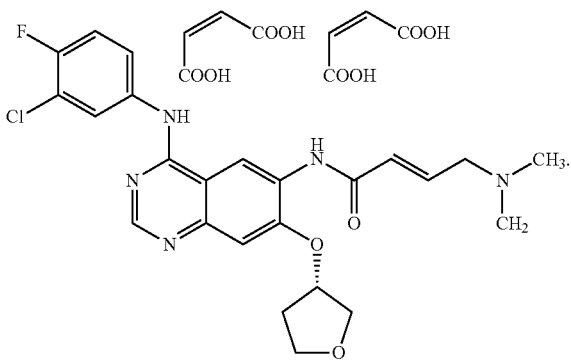

GILOTRIF™ is indicated for the first-line treatment of patients with metastatic non-small cell lung cancer (NSCLC) whose tumors have epidermal growth factor receptor (EGFR) exon 19 deletions or exon 21 (L858R) substitution mutations as detected by an FDA-approved test.

Crystalline forms of afatinib and salts thereof are described in International Publication Nos. WO/2005037824, WO2012/121764, WO2013/052157, WO2015/103456, WO2016/027243, WO2016/001844, WO2016/051380, and WO2016/079313. Afatinib dimaleate Form A, as disclosed in International Publication No. WO/2005037824, completely converts to a hydrated species under 40° C., 75% RH conditions by 11 days. The occurrence of different crystalline forms of afatinib and salts thereof gives rise to a variety of polymorphs having distinct crystal structures and physical properties like melting point, thermal behaviors. Polymorphic forms of the compound are important in that the forms having desirable characteristics, such as ease of handling, ease of processing, ease of formulating, storage stability, ease of purification, improved dissolution or bioavailability, or form that facilitates conversion to another desirable polymorphic form. Thus, a new polymorphic form of afatinib dimaleate is useful for providing the compound having desirable characteristics. For at least these reasons, there is a need for additional polymorphic forms of afatinib dimaleate.

SUMMARY OF THE DISCLOSURE

The present invention is directed to a novel crystalline, hydrated form of afatinib dimaleate having about 2 to 3 molecules of water, designated herein as Form Z. The present invention is further directed to processes for the preparation of Form Z. The present invention also is directed to a pharmaceutical composition comprising Form Z, and a method for treating disease using Form Z.

DETAILED DESCRIPTION OF THE DISCLOSURE

Figure 1:
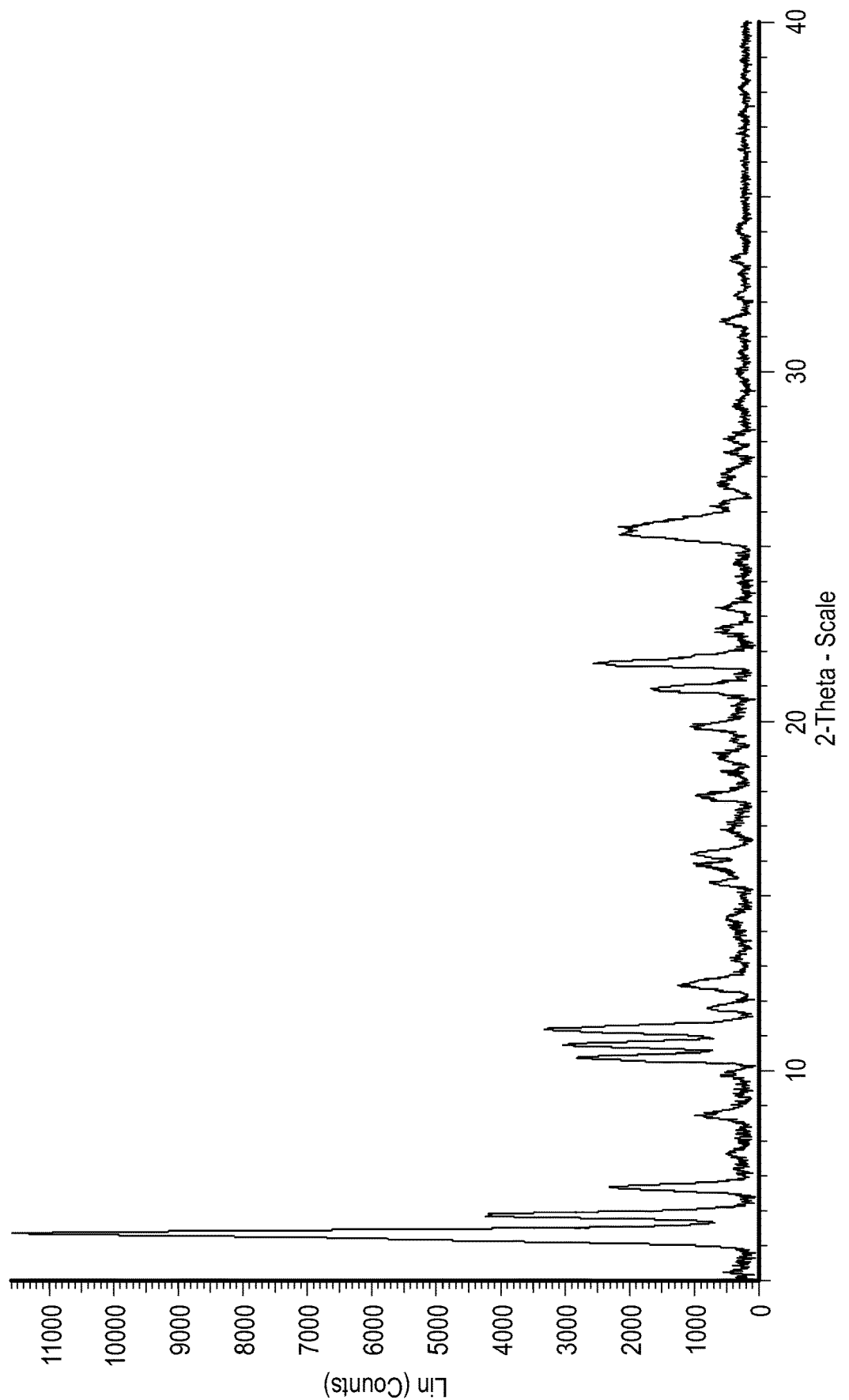
FIG. 1 provides a representative XRPD pattern of Form Z, expressed in terms of ° 2θ.

The present disclosure is directed to a novel crystalline, hydrated form of afatinib dimaleate having about 2 to 3 molecules of water, designated herein as Form Z; a pharmaceutical composition comprising the form, process for its preparation, and its use for treating a patient with a physiological condition in need of treatment, as herein described in detail.

As used herein and unless otherwise specified, the terms "about" and "approximately," when used in connection with a numeric value or a range of values which is provided to characterize a particular solid form, e.g., a specific temperature or temperature range, such as, e.g., that describing a DSC or TGA thermal event, including, e.g., melting, dehydration, desolvation or glass transition events; a mass change, such as, e.g., a mass change as a function of temperature or humidity; a solvent or water content, in terms of, e.g., mass or a percentage; or a peak position, such as, e.g., in analysis by IR or Raman spectroscopy or XRPD; indicate that the value or range of values may deviate to an extent deemed reasonable to one of ordinary skill in the art while still describing the particular solid form.

As used herein and unless otherwise specified, the term "pharmaceutical composition" is intended to encompass the a pharmaceutically effective amount of Form Z and pharmaceutically acceptable excipient. As used herein, the term "pharmaceutical compositions" includes pharmaceutical compositions such as tablets, pills, powders, liquids, suspensions, emulsions, granules, capsules, suppositories, or injection preparations.

As used herein and unless otherwise specified, the term "crystalline" and related terms used herein, when used to describe a compound, substance, modification, material, component or product, unless otherwise specified, mean that the compound, substance, modification, material, component or product is substantially crystalline as determined by X-ray diffraction. See, e.g., Remington: The Science and Practice of Pharmacy, 21st edition, Lippincott, Williams and Wilkins, Baltimore, Md. (2005); The United States Pharmacopeia, 23rd ed., 1843-1844 (1995).

As used herein and unless otherwise specified, the term "excipient" refers to a pharmaceutically acceptable organic or inorganic carrier substance. Excipients may be natural or synthetic substances formulated alongside the active ingredient of a medication, included for the purpose of bulking-up formulations that contain potent active ingredients (thus often referred to as "bulking agents," "fillers," or "diluents"), or to confer a therapeutic enhancement on the active ingredient in the final dosage form, such as facilitating drug absorption or solubility. Excipients can also be useful in the manufacturing process, to aid in the handling of the active substance, such as by facilitating powder flowability or non-stick properties, in addition to aiding in vitro stability such as prevention of denaturation over the expected shelf life.

As used herein and unless otherwise specified, the term "patient" refers to an animal, preferably a mammal, most preferably a human, who has been the object of treatment, observation or experiment. Preferably, the patient has experienced and/or exhibited at least one symptom of the disease or disorder to be treated and/or prevented. Further, a patient may not have exhibited any symptoms of the disorder, disease or condition to be treated and/prevented, but has been deemed by a physician, clinician or other medical professional to be at risk for developing said disorder, disease or condition.

As used herein and unless otherwise specified, the terms "polymorph," "polymorphic form" or related term herein, refer to a crystal form of a molecule, or salt thereof that can exist in two or more forms, as a result different arrangements or conformations of the molecule or salt thereof ions in the crystal lattice of the polymorph.

As used herein and unless otherwise specified, the terms "treat," "treating" and "treatment" refer to the eradication or amelioration of a disease or disorder, or of one or more symptoms associated with the disease or disorder. In certain embodiments, the terms refer to minimizing the spread or worsening of the disease or disorder resulting from the administration of one or more therapeutic agents to a patient with such a disease or disorder. In some embodiments, the terms refer to the administration of a compound provided herein, with or without other additional active agents, after the onset of symptoms of the particular disease. Afatinib dimaleate is indicated for the first-line treatment of patients with metastatic non-small cell lung cancer (NSCLC) whose tumors have epidermal growth factor receptor (EGFR) exon 19 deletions or exon 21 (L858R) substitution mutations. Afatinib dimaleate is also indicated for the treatment of patients with metastatic squamous NSCLC progressing after platinum-based chemotherapy. GILOTRIF™ is available as 40 mg tablets, 30 mg tablets and 20 mg tablets. The recommended dose of GILOTRIF™ is 40 mg, orally, once daily. The recommended dose in patients with severe renal impairment (estimated glomerular filtration rate [eGFR*] 15 to 29 mL/min/1.73 m$^2$) is 30 mg orally, once daily.

Techniques for characterizing crystal and amorphous forms include, but are not limited to differential scanning calorimetry (DSC), thermal gravimetric analysis (TGA), X-ray powder diffractometry (XRPD), proton nuclear magnetic resonance ($^1$H-NMR) and Optical Microscopy.

DSC data were collected using a TA Instruments Q10 DSC. Approximately, samples (2-8 mg) were placed in unsealed but covered hermetic alodined aluminum sample pans and scanned from about 30 to about 300° C. at a rate of about 10° C./min under a nitrogen purge of about 50 mL/min.

TGA data were collected using a TA Instruments TGA Q500. Approximately, samples (5-10 mg) were placed in an open, pre-tared aluminum sample pan and scanned from about 25 to about 300° C. at a rate of about 10° C./min using a nitrogen purge at about 60 mL/min.

XRPD patterns were obtained using a Bruker D8 Advance equipped with a Cu Kα radiation source (λ=1.54 Å), a 9-position sample holder and a LYNXEYE super speed detector. Samples were placed on zero-background, silicon plate holders for analysis. One skilled in the art would recognize that the ° 2θ values and the relative intensity values are generated by performing a peak search on the measured data and the d-spacing values are calculated by the instrument from the ° 2θ values using Bragg's equation. One skilled in the art would further recognize that the relative intensity for the measured peaks may vary as a result of sample preparation, orientation and instrument used, for example.

$^1$H-NMR data were collected using a Bruker Avance 300 MHz NMR equipped with TopSpin software. Samples were prepared by dissolving the compound in deuterated dimethylsulfoxide with 0.05% (v/v) tetramethylsilane (TMS). Spectra were collected at ambient temperature. The number of scans was 16 for $^1$H-NMR.

Form Z is a unique crystalline phase. Form Z is an off-white solid material. Form Z is a species containing about 2 to 3 molecules of water. Form Z is stable under exposure to water.

The present disclosure also encompasses pharmaceutical compositions comprising Form Z. Pharmaceutical compositions containing Form Z may be prepared according to International Publication Nos. WO2009/147238 and WO2011/003853, which are incorporated herein by reference in their entireties.

The present disclosure provides for a method of treating disease by administering to a patient, in need thereof, pharmaceutical compositions comprising Form Z. Afatinib dimaleate is indicated for the first-line treatment of patients with metastatic non-small cell lung cancer (NSCLC) whose tumors have epidermal growth factor receptor (EGFR) exon 19 deletions or exon 21 (L858R) substitution mutations. Afatinib dimaleate is also indicated for the treatment of patients with metastatic squamous NSCLC progressing after platinum-based chemotherapy.

The dosage of the pharmaceutical compositions may be varied over a wide range. Optimal dosages and dosage regimens to be administered may be readily determined by those skilled in the art, and will vary with the mode of administration, the strength of the preparation and the advancement of the disease condition. In addition, factors associated with the particular patient being treated, including patient's sex, age, weight, diet, physical activity, time of administration and concomitant diseases, will result in the need to adjust dosages and/or regimens. Afatinib dimaleate, marketed under the name GILOTRIF™, is available as 40 mg tablets, 30 mg tablets and 20 mg tablets. The recommended dose of GILOTRIF™ is 40 mg, orally, once daily. The recommended dose in patients with severe renal impairment is 30 mg orally, once daily.

EXAMPLES

Form Z according to the invention may be prepared directly or indirectly from afatinib or afatinib dimaleate. Examples 1-4, which follow herein, provide embodiments of the preparation of the Form Z.

Example 1

Preparation of Form Z

About 90 mg of afatinib dimaleate and about 1 mL of 2-butanol are slurried for about 48 hours. About 100 μL of water is added to the slurry at about 25° C. An off-white precipitate is formed. The dried material is analyzed and identified as Form Z.

Example 2

Preparation of Form Z

About 325 mg of afatinib dimaleate and about 6 mL of 2-butanol are slurried for about 2 hours. About 1 mL of water is added to the slurry at about 25° C. A small aliquot is removed and identified as Form Z. The remaining slurry is stirred for about 21 days. The isolated, dried material is analyzed and identified as afatinib Form Z.

Example 3

Preparation of Form Z

About 225 mg of afatinib free base is added to about 15 ml of 2-butanol to make an afatinib free base solution. About 113 mg of maleic acid is added to about 1 mL of water to make an aqueous solution of maleic acid. The aqueous solution of maleic acid is added to the afatinib free base solution at about 25° C. After about 20 minutes, an off-white precipitate is formed. After about 48 hours, the dried material is analyzed and identified as Form Z.

Example 4

Preparation of Form Z

About 225 mg of afatinib free base is added to about 11 ml of 2-butanol to make an afatinib free base solution. About 113 mg of maleic acid is added to about 1 mL of water to make an aqueous solution of maleic acid. The aqueous solution of maleic acid is added to the afatinib free base solution at about 25° C. An off-white precipitate is formed overnight. After about 48 hours, the dried material is analyzed and identified as Form Z.

Form Z is stable under exposure to water vapor under ambient conditions (about 25° C., >90% RH) for about 3 days and is at stable for over 19 days at about 40° C., 75% RH. Afatinib dimaleate Form A, as disclosed in International Publication No. WO/2005037824, completely converts to a hydrated species under 40° C., 75% RH conditions by 11 days. Thus, Form Z is more stable than afatinib dimaleate Form A.

Form Z is characterized by its XRPD pattern peaks and/or d-spacing values. An average of the XRPD pattern peaks and d-spacing values for Form Z are listed in Table 1 below. FIG. 1 is a representative XPRD pattern for a representative sample of Form Z made according to Example 4.

TABLE 1

Average Peak List for Form Z diffractogram

| Angle (2θ) degree | Intensity % | d value (Å) |
|---|---|---|
| 5.27 | 100.00 | 16.77 |
| 5.82 | 40.43 | 15.18 |
| 11.11 | 34.65 | 7.95 |
| 21.63 | 31.65 | 4.10 |
| 25.38 | 30.15 | 3.51 |
| 10.69 | 28.78 | 8.27 |
| 10.30 | 27.65 | 8.58 |
| 6.60 | 24.60 | 13.38 |
| 20.87 | 22.38 | 4.25 |
| 12.40 | 16.13 | 7.13 |
| 19.80 | 15.33 | 4.48 |
| 16.15 | 13.85 | 5.48 |
| 17.77 | 13.48 | 4.99 |
| 8.66 | 13.05 | 10.20 |
| 15.80 | 11.58 | 5.60 |
| 11.74 | 11.28 | 7.53 |
| 15.30 | 11.23 | 5.79 |
| 23.25 | 10.78 | 3.82 |
| 22.60 | 10.60 | 3.93 |
| 31.41 | 10.60 | 2.85 |
| 26.72 | 10.57 | 3.33 |
| 33.18 | 10.47 | 2.70 |
| 28.06 | 10.30 | 3.18 |
| 27.66 | 10.10 | 3.22 |
| 27.03 | 9.98 | 3.30 |
| 7.57 | 9.33 | 11.67 |
| 9.83 | 7.77 | 8.99 |

Figure 2:
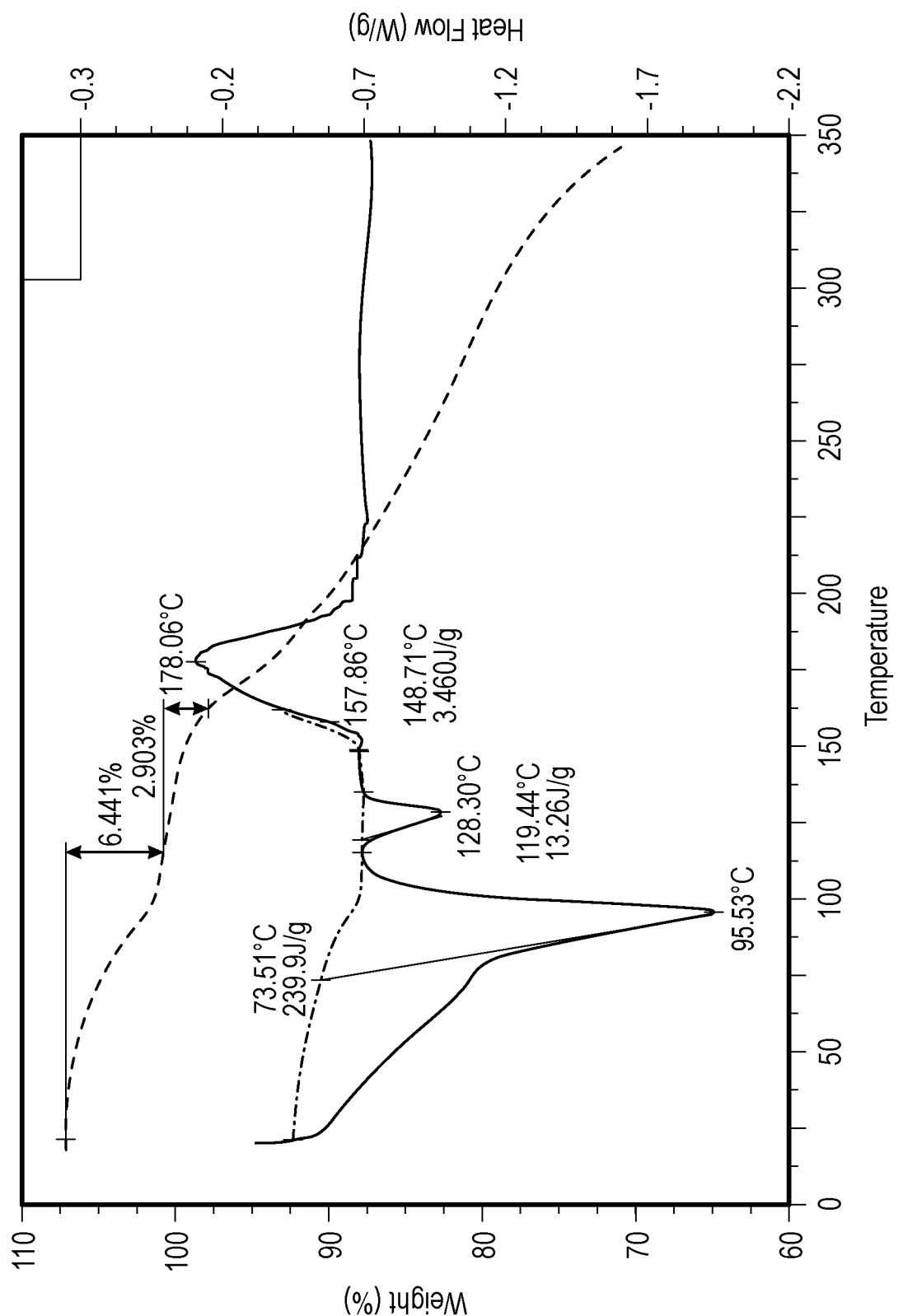
FIG. 2 provides a representative Differential Scanning Calorimetry ("DSC") and Thermal Gravimetric Analysis ("TGA") plot of Form Z.

A DSC thermogram and a TGA plot of Form Z made according to Example 4, FIG. 2, shows a thermal event at about 95.5° C. and about 128.3° C., and a weight loss of about 6.4% when heated to about 100° C.

Figure 3:
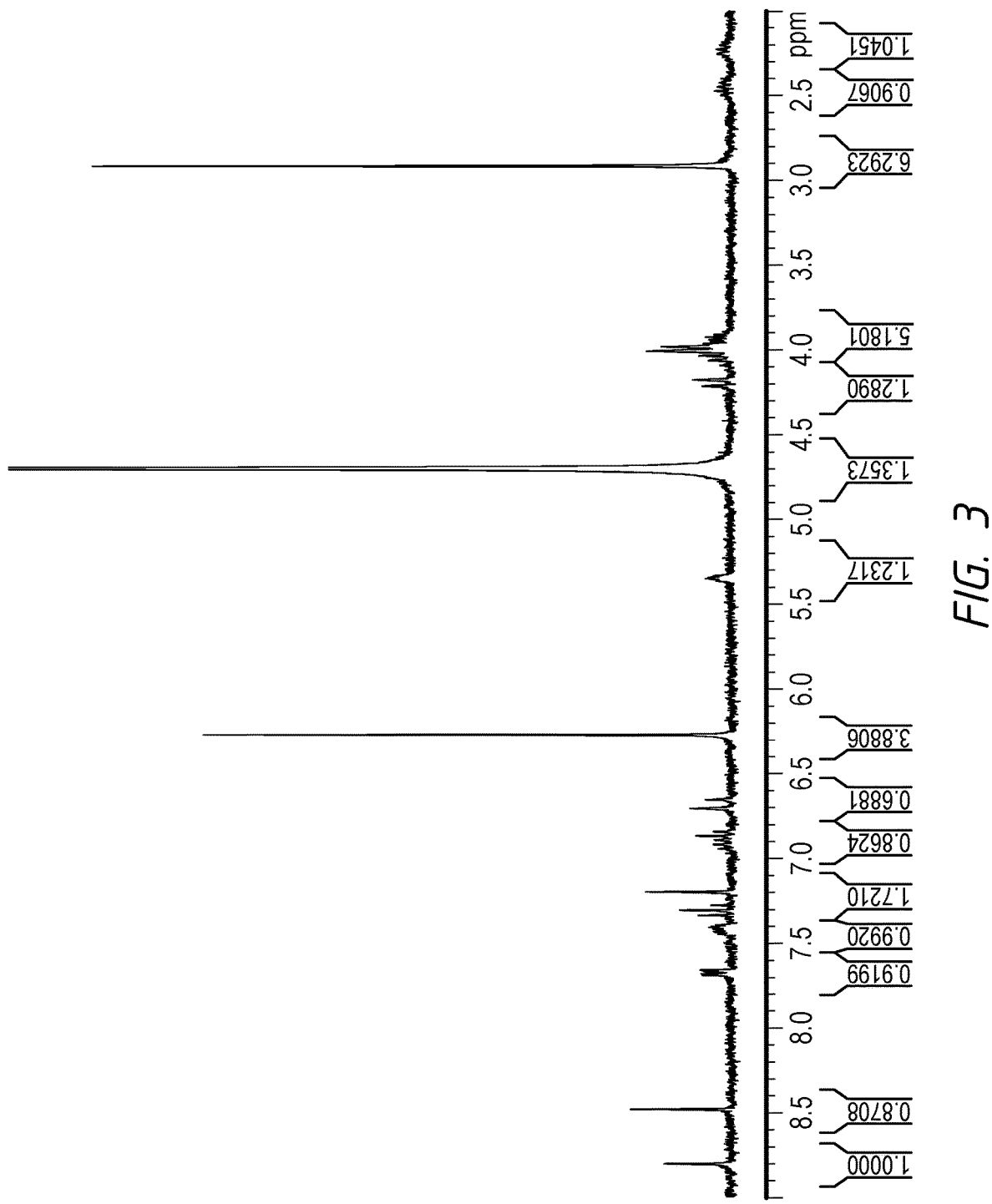
FIG. 3 provides a representative Proton Nuclear Magnetic Resonance ($^1$H-NMR) plot of Form Z.

FIG. 3 is a representative Proton Nuclear Magnetic Resonance ($^1$H-NMR) plot of Form Z made according to Example 4.

The above examples are set forth to aid in the understanding of the disclosure, and are not intended and should not be construed to limit in any way the disclosure set forth in the claims which follow hereafter. Although illustrated and herein described with reference to certain specific embodiments, the present disclosure is nevertheless not intended to be limited to the details shown, but various modifications may be made therein without departing from the spirit of the disclosure.

What is claimed is:

1. A crystalline, hydrated form of afatinib dimaleate having about 2 to 3 molecules of water, designated as Form Z, wherein the Form Z comprises X-ray powder diffraction peaks, in terms of 2-theta, at about 11.1, about 10.7 and about 6.6.

2. Form Z according to claim 1, wherein the Form Z further comprises one or more X-ray powder diffraction peaks, in terms of 2-theta, at about 5.3, about 5.8 and about 21.6.

3. Form Z according to claim 2, wherein the Form Z further comprises one or more X-ray powder diffraction peaks, in terms of 2-theta, at about 25.4, about 10.3 and about 20.9.

4. Form Z according to claim 1, wherein the Form Z comprises one or more X-ray powder diffraction peaks at d-spacing, in terms of Angstroms, at about 8.0, about 8.3 and about 13.4.

5. Form Z according to claim 4, wherein Form Z further comprises one or more X-ray powder diffraction peaks at d-spacing, in terms of Angstroms, at about 16.8, about 15.2 and about 4.1.

6. Form Z according to claim 5, wherein Form Z further comprises one or more X-ray powder diffraction peaks, at d-spacing, in terms of Angstroms, at about 3.5, about 8.6 and about 4.3.

7. Form Z according to claim 1, wherein Form Z is characterized by an endothermic event at about 95.5° C., as measured by differential scanning calorimetry.

8. Form Z according to claim 1, wherein Form Z is characterized by an endothermic event at about 128.3° C., as measured by differential scanning calorimetry.

9. A pharmaceutical composition comprising a pharmaceutically effective amount of Form Z according to claim 1 and pharmaceutically acceptable excipient.

10. A method of treating disease in a patient comprising administering a pharmaceutical composition according to claim 9 to the patient in need thereof.

11. A method of treating disease according to claim 10, wherein the disease is lung cancer.

12. A method of making Form Z according to claim 1, comprising exposing afatinib dimaleate to 2-butanol and water to yield Form Z.

13. A method of making Form Z according to claim 1, comprising exposing a solution comprising afatinib free base and 2-butanol to an aqueous solution of maleic acid to yield Form Z.

* * * * *